United States Patent
Fomitchov et al.

(10) Patent No.: US 8,103,329 B2
(45) Date of Patent: Jan. 24, 2012

(54) SYSTEM AND METHOD FOR IMAGING BASED ON ULTRASONIC TAGGING OF LIGHT

(75) Inventors: Pavel Alexeyevich Fomitchov, New York, NY (US); Kajoli Banerjee Krishnan, Bangalore (IN); Stephen Johnson Lomnes, Albany, NY (US); Floribertus P. M. Heukensfeldt Jansen, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 1346 days.

(21) Appl. No.: 11/254,266

(22) Filed: Oct. 20, 2005

(65) Prior Publication Data

US 2006/0058685 A1    Mar. 16, 2006

Related U.S. Application Data

(63) Continuation-in-part of application No. 10/714,734, filed on Nov. 17, 2003, now abandoned.

(51) Int. Cl.
*A61B 5/05* (2006.01)
(52) U.S. Cl. ......... 600/407; 600/437; 600/473; 600/476
(58) Field of Classification Search .......... 600/407, 600/476, 437, 473
See application file for complete search history.

(56) References Cited

U.S. PATENT DOCUMENTS

| | | | |
|---|---|---|---|
| 5,174,298 A | 12/1992 | Dolfi et al. ............ 128/665 |
| 5,203,339 A * | 4/1993 | Knuttel et al. ........... 600/425 |
| 5,212,667 A | 5/1993 | Tomlinson, Jr. et al. ..... 367/7 |
| 5,451,785 A * | 9/1995 | Faris ................. 250/330 |
| 5,919,140 A * | 7/1999 | Perelman et al. ......... 600/476 |
| 5,999,836 A * | 12/1999 | Nelson et al. ............ 600/407 |
| 6,091,983 A * | 7/2000 | Alfano et al. ........... 600/431 |
| 6,321,111 B1 * | 11/2001 | Perelman et al. ......... 600/477 |
| 6,424,857 B1 * | 7/2002 | Henrichs et al. .......... 600/431 |
| 6,530,944 B2 * | 3/2003 | West et al. .............. 607/88 |
| 6,738,653 B1 | 5/2004 | Sfez et al. .............. 600/322 |
| 7,231,243 B2 * | 6/2007 | Tearney et al. ........... 600/407 |
| 7,889,348 B2 * | 2/2011 | Tearney et al. ........... 356/451 |
| 2003/0100824 A1 * | 5/2003 | Warren et al. ............ 600/407 |
| 2004/0087861 A1 | 5/2004 | Jiang .................... 600/473 |
| 2004/0127783 A1 * | 7/2004 | Kruger ................... 600/407 |

OTHER PUBLICATIONS

Lihong V. Wang, "Ultrasound-mediated biophotonic imaging: A review of acousto-optical tomography and photo-acoustic tomography", IOS Press Disease Markers 19 (2003,2004) pp. 123-138.

T. Khan and H. Jiang, "A new diffusion approximation to the radiative transfer equation for scattering media with spatially varying refractive indices", Journal of Optics A: Pure and Applied Optics 5 (2003) pp. 137-141.

A McWilliams et al., Innovative molecular and imaging approaches for the detection of lung cancer and its precursor lesions, Oncogene (2002) 21, pp. 6949-6959, Available at www.nature.com/onc.

* cited by examiner

*Primary Examiner* — Tse Chen
*Assistant Examiner* — Baisakhi Roy
(74) *Attorney, Agent, or Firm* — Jason K. Klindtworth (57) ABSTRACT

A technique is provided for imaging based on localization of fluorescence in a medium. The technique includes illuminating the medium with an excitation light to excite fluorescence, scanning the medium at a plurality of locations via an ultrasonic beam, modulating a portion of the emitted light from the fluorescence via the ultrasonic beam at each of the plurality of locations, differentially detecting the modulated light at a boundary of the medium, and reconstructing an image from the detected signal.

33 Claims, 7 Drawing Sheets

SYSTEM AND METHOD FOR IMAGING BASED ON ULTRASONIC TAGGING OF LIGHT

CROSS REFERENCE TO RELATED APPLICATIONS

This application is a Continuation-in-Part of U.S. patent application Ser. No. 10/714,734, filed on Nov. 17, 2003 now abandoned, which is herein incorporated by reference.

BACKGROUND

The invention relates generally to the field of imaging and more specifically, to the field of acousto-optic imaging.

Various imaging techniques have been developed for use in a wide range of applications. For example, in modern healthcare facilities, non-invasive imaging systems are often used for identifying, diagnosing, and treating physical conditions. Medical imaging typically encompasses the different non-invasive techniques to image and visualize the internal structures and/or functional behavior (such as chemical or metabolic activity) of organs and tissues within a patient. Currently, a number of modalities exist for medical diagnostic and imaging systems, each typically operating on different physical principles to generate different types of images and information. These modalities include ultrasound systems, computed tomography (CT) systems, X-ray systems (including both conventional and digital or digitized imaging systems), positron emission tomography (PET) systems, single photon emission computed tomography (SPECT) systems, and magnetic resonance (MR) imaging systems.

Another imaging modality is optical imaging, which operates by propagating light of certain wavelengths through a patient and generating an image based on the propagated light. Different wavelengths of light, including near infrared (NIR) wavelengths in the 700-1000 nm window, may be used to measure optical properties of tissue. Optical properties of tissues may then be used as a contrast mechanism for diagnostic medical imaging (i.e., as a basis for image generation). NIR light is both absorbed and scattered in a turbid medium such as biological tissue. However, scattering greatly dominates absorption in this wavelength range. Light sources and detectors may typically be located at the boundary of the tissue-air interface. The transport of the photon density waves from the source to the detectors and the consequent change in their amplitude and phase can be tracked in tissue with a known distribution of optical properties using a forward model. The inverse problem involves the use of measurements made on the tissue-air interface to reconstruct the spatial map of absorption coefficients in the interior of the tissue. Such values may be used to develop images of the features of internal tissues.

Although conceptually simple, the ill-posed nature and the non-unique solution to the problem of optical reconstruction is further complicated by non-linearity due to scattering, low signals due to absorption, and limited contrast offered by different tissue types. Despite improvements possible with endogenous fluorescence contrast, optically reconstructed images are limited in sensitivity and spatial resolution due to the smearing of endogenous contrast through scattering and absorption. Due to light absorption and scattering by the imaged tissue, diffuse optical imaging typically has relatively poor spatial resolution and anatomical registration. For example, when optical imaging using endogenous contrast is employed for cancer detection, the imaging technique suffers from low or reduced sensitivity and specificity.

Several diffuse optical reconstruction techniques have been formulated and employed in an effort to overcome limitations of diffuse optical imaging, such as those discussed above. Different broad conventional approaches to tackle the complexity of the diffuse optical reconstruction problem are based on linearizing the problem, using multiple wavelengths, measuring the time varying properties of diffusion density waves over ranges of frequencies, detecting ultrasound generated by thermo-acoustic expansion of absorbed light, acoustically modulating the light from the illumination source in situ, employing exogenous fluorescent probes to enhance image contrast, and adding a priori anatomical and/or functional information about the sample from another modality to constrain the reconstruction.

For example, techniques that combine ultrasonic acoustics and light propagation in tissue are promising ways of improving the spatial resolution of diffuse optical imaging. Examples of such techniques include photo-acoustic imaging techniques and acousto-optic imaging techniques. Photo-acoustic imaging techniques typically generate maps of relative optical absorption of a tissue or sample at the wavelengths of excitation light, with strong signals being generated by stronger absorbers. This technique is amenable to generating images of both endogenous and exogenous absorbers. Acousto-optic imaging techniques, by comparison, also generate maps of relative absorption by propagating coherent light into the scattering tissue where the propagated light, through constructive and destructive interference, establishes a speckle field. An acoustic field is applied to the tissue, thereby applying microscopic movement of scattering elements, changing the speckle field in a time-varying manner. These time varying components of the optical signal are inspected and assessments of the spatial distribution of absorption are made. This technique is therefore also amenable to endogenous and exogenous absorption contrast. However, substantial amounts of absorbing material are required to result in a measurable change in the detected signals. As a result, the imaging paradigm is equivalent to measuring a small change in contrast on a largely varying background. The use of exogenous fluorescent probes is advantageous in providing improved sensitivity as one can filter the wavelength of light that is allowed to be extremely selective to fluorescent emission. This is equivalent to measuring a small signal on a flat background. However, fluorescence is typically not a useable mechanism in photo-acoustic imaging, since good fluorescent dyes make poor photo-acoustic dyes, or in acousto-optic imaging, where the incoherent light emitted from fluorescence is not modulated via the same mechanisms as the coherent light and hence does not demonstrate the same interference.

The ill-posed nature of the reconstruction problem may be significantly reduced by a hybrid imaging system that combines the sensitivity of optical imaging (further improved via fluorescence) with the spatial resolution of ultrasound (acoustic imaging). The incoherent light from fluorescence propagating through the scattering and absorbing tissue medium would be modulated during its passage through the focal region of an externally applied focused ultrasound wave. Ultrasonic excitation from an internal or external source may therefore be used to overcome the relatively low resolution of the optical imaging system. However, it has been found that the strength of the modulated signal rapidly deteriorates with increase in depth of the scattering medium (tissue) due to scattering. This therefore places greater requirements on detector sensitivity required to perform deep tissue imaging.

It is therefore desirable to improve the sensitivity in acousto-optic imaging while taking advantage of its improved spatial resolution. It is also desirable to provide improved acousto-optic coupling mechanisms for incoherent light in turbid media that would enable deeper tissue imaging with better sensitivity and resolution. Further, it is desirable to provide acousto-optic imaging system with improved scanning speed and signal-to-noise ratio.

BRIEF DESCRIPTION

Briefly, in accordance with one aspect of the technique, a method is provided for localization of fluorescence in a medium. The method provides for illuminating the medium with an excitation light to excite the fluorescence, modulating a portion of the emitted light from the fluorescence within the medium via an ultrasonic beam, and differentially detecting the modulated light at a surface of the medium. Systems and computer programs that afford such functionality may be provided by the present technique.

In accordance with another aspect of the technique, a method is provided for imaging. The method provides for illuminating a medium with an excitation light to excite fluorescence, scanning the medium at a plurality of locations via an ultrasonic beam, modulating a portion of the emitted light from the fluorescence via the ultrasonic beam at each of the plurality of locations, differentially detecting the modulated light at a boundary of the medium, and reconstructing an image from the detected signal. Here again, systems and computer programs affording such functionality may be provided by the present technique.

In accordance with another aspect of the technique, a system is provided for localization of fluorescence in a medium. The system includes an excitation light source for illuminating the medium, a fluorescent agent within a preselected region of the medium for absorbing the excitation light and emitting light in a near infrared spectral region via fluorescence, and an ultrasonic scanning system for generating ultrasonic beam. The ultrasonic beam modulates a portion of the emitted light from the fluorescent agent. The system also includes an optical detection system for differentially detecting the modulated light.

In accordance with a further aspect of the technique, an imaging system is provided. The imaging system includes an excitation light source for illuminating a medium, a fluorescent agent within a preselected region of the medium for absorbing the excitation light and emitting light in a near infrared spectral region via fluorescence, and an ultrasonic scanning system for generating ultrasonic beam. The ultrasonic beam scans the medium at a plurality of locations and modulates a portion of the emitted light from the fluorescent agent at each of the plurality of locations. The imaging system also includes an optical detection system for differentially detecting the modulated light, and a data processing system for reconstructing an image from the detected signal.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques relate to acousto-optic imaging based on localization of fluorescence in a turbid medium (simultaneously absorbing and scattering medium). In various embodiments of the present technique, systems and methods will be employed for localizing an object of interest, e.g., a lesion labeled with a fluorescent dye, in a turbid medium, e.g., biological tissue.

Figure 1:
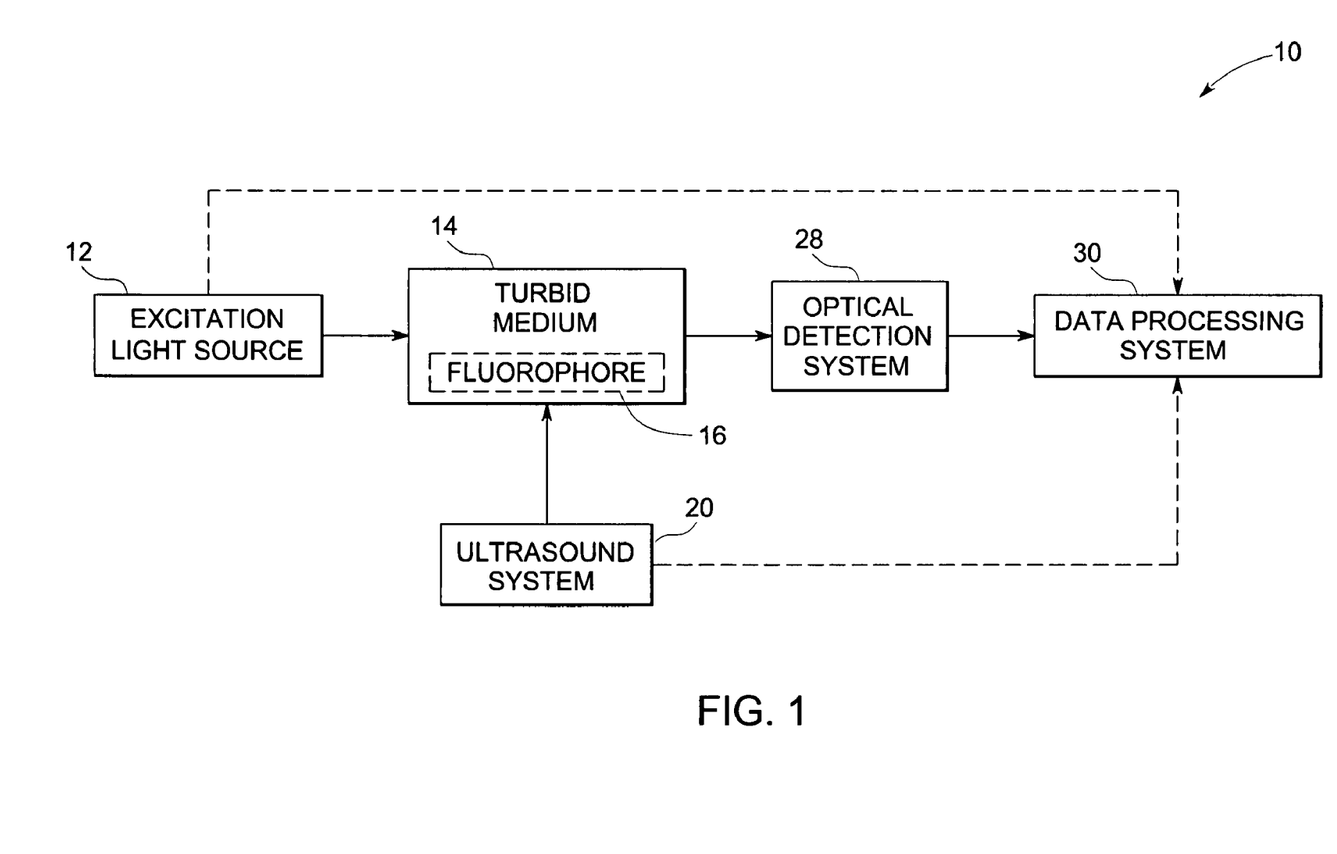
FIG. 1 is a block diagram of an exemplary imaging system for acousto-optic imaging in accordance with aspects of the present technique.
Figure 2:
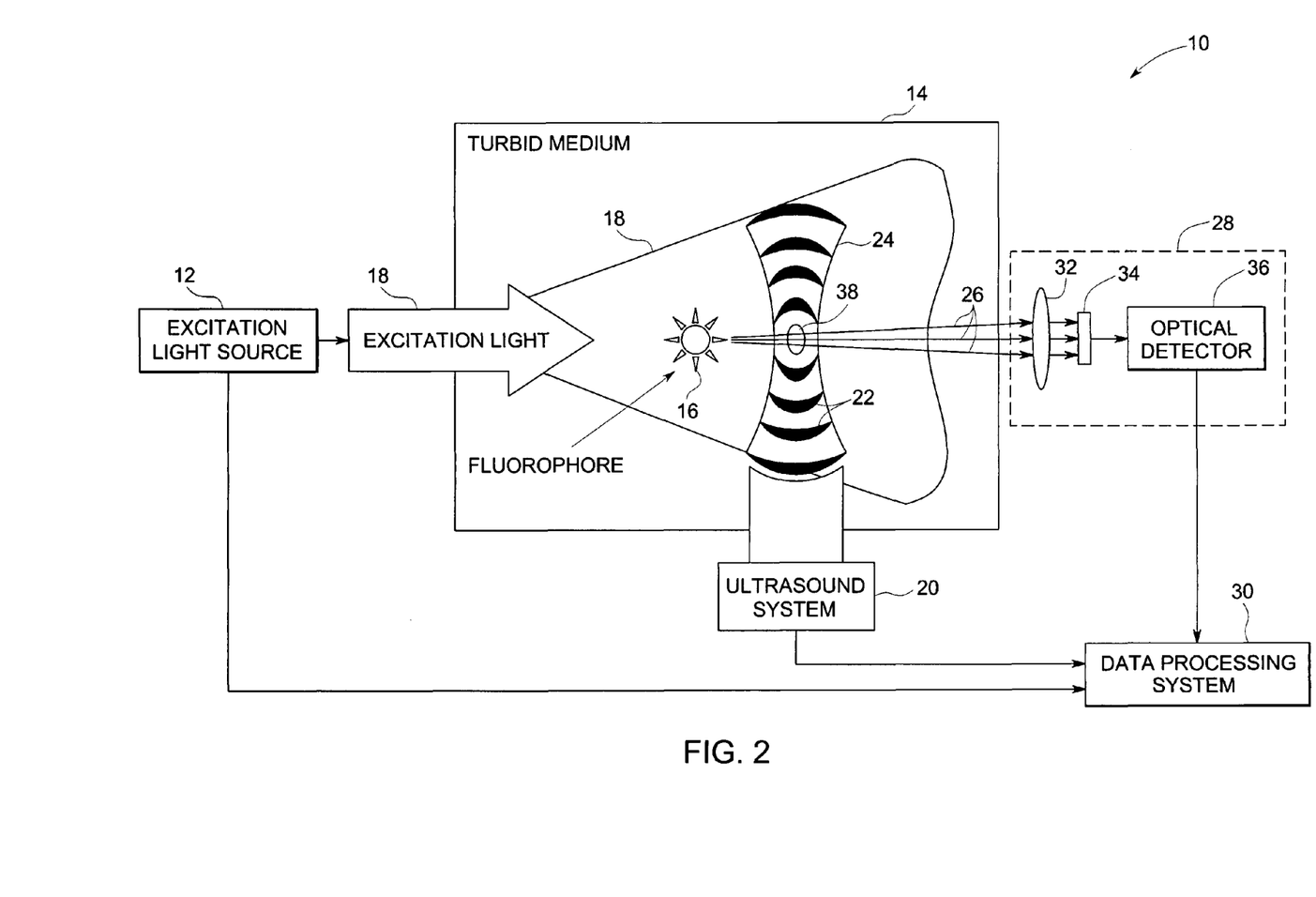
FIG. 2 is an exemplary imaging system for illustrating the principle of acoustic modulation of fluorescent light for acousto-optic imaging.

Referring now to FIG. 1 and FIG. 2, an exemplary acousto-optic imaging system 10 generally includes an excitation light source 12 for illuminating a turbid medium 14, including an object of interest 16, with radiant energy, e.g., light 18. The light 18 excites a fluorophore contrast agent present in the object of interest 16 to cause fluorescence. The system 10 further includes an ultrasound generation system 20 for generating ultrasound pulses or an ultrasonic beam 22 directed into the turbid medium 14, thereby inducing volumetric changes of optical properties of the medium, such as refractive index, and thus creating an acoustic lens 24. The light 26 emitted from the object of interest 16 (from fluorescence) is deflected or modulated by the acoustic lens 24. The acousto-optic imaging system 10 further includes an optical detection system 28 for detecting the radiant energy, e.g., light, 26 deflected by the acoustic lens 24. Alternatively, the ultrasound generation system 20 will induce the acoustic lens 24 to modulate the excitation light 18 before it reaches the object of interest 16. The modulated light will then excite the fluorophore contrast agent in the object of interest, which will emit light (fluorescence) to be detected by the optical detection system 28.

The optical detection system 28 may further include a light collection and delivery system 32 such as optical lens for collecting the emitted light, one or more optical filters 34 for filtering the light and allowing transmission of fluorescent emission and an optical detector 36 for converting optical signals to electrical signals capable of being read by a data processing system 30. In certain embodiments, the light collection and delivery system 32 consists of an optical fiber and/or a fiber collimator for collecting light from the turbid medium 14 and delivering the collected light to the optical detector 36. In certain embodiments, the optical detection system 28 may be configured to detect the modulated light differentially based on certain parameters described in detail below. The data processing system 30 collects data from the optical detection system 28 to construct an image of the turbid medium 14 and controls the overall operations of the excitation light source 12, the ultrasound generation system 20 and the optical detection system 28.

Prior to or during the imaging procedure, a fluorescent optical contrast agent is introduced into the turbid medium 14, e.g., biological tissue. The fluorescent contrast agent may preferentially bind to an object of interest 16, e.g., diseased tissue, and thus may have disease or functional specificity. The fluorescent contrast agent may be one or more or a derivative of the following: Indocyanine green (ICG), a member of the Cy family of dyes, the IR-78 dye, peptide, cyanine, squarilium, croconium, merocyanine or oxonol dye molecule, lanthanide metal chelate, quantum dot, metal nanocluster or any other fluorophore that emits light in the NIR region. The fluorescent contrast agent will absorb and emit light 26 in the "transparency window" of biological tissue, which is between 700-900 nm where absorption of light in tissue is minimized. In other applications, it may be useful to operate anywhere in the range from 400-2000 nm for use with light emitting agents that operate in these wavelengths.

The optical excitation source 12 with a spectral output tuned to a maximal absorption wavelength of the fluorescent dye is used to excite the fluorescence. The excitation light source 12 may include any light source such as a laser, laser diode, light emitting diode (LED), or a lamp (e.g., halogen lamp, incandescent lamp, arc lamp, high intensity discharge lamp etc.). In one embodiment, the excitation light is an ultra-short laser pulse or a sequence of such pulses. Alternatively, in certain embodiments, multiple sources deliver the light via optical fiber or fiber optic bundles to form an array of localized illumination spots that may be illuminated simultaneously or in a sequence. The optical source can be operated in continuous wave (CW) mode, intensity modulated wave mode, or pulsed wave mode. The frequency of intensity modulation and pulse repetition rate may be equal or fractional with respect to an ultrasonic frequency of the ultrasound generation system 20.

When excitation photons 18 reach the fluorescent dye in the object of interest 16, e.g., a lesion, localized in a volume of biological tissue, the fluorescence will re-emit optical radiation 26 at a longer wavelength and acts as an omnidirectional optical source. As will be appreciated by one skilled in the art, the emitted light 26 from fluorescence comprises of ballistic photons, snake-like photons, and/or diffused photons.

A focused or a wide, plane ultrasonic beam 22 is then formed using the ultrasonic generation system 20. The ultrasonic generation system 20 may include, for example, (i) a piezoelectric ultrasonic transducer (PZT) coupled to an arbitrary function generator and a high power RF amplifier; (ii) an ultrasonic scanning phased array, (iii) a capacitive ultrasound transducer; or (iv) a laser photoacoustic generator. The generated ultrasonic beam 22 is transmitted into and scanned throughout the volume of the turbid medium (tissue) 14. The ultrasonic generation may be performed in CW mode, or in pulsed wave mode using single frequency or frequency-swept tonebursts, or a short single broadband pulse. The ultrasonic beam may be configured, for example, as a single ultrasonic focal spot; an array of focal spots situated along a single line; a line focused beam oriented along optical source-to-receiver axis; superposition of two or more ultrasonic beams to form an acoustic interference pattern at the same frequency; superposition of two or more ultrasonic beams to form an acoustic interference pattern at different frequencies, or a planar ultrasonic beam.

The generated ultrasonic wave 22 changes the refractive index of the turbid medium (tissue) 14 via an elasto-optic effect. The amount of refractive index modulation depends on the acoustic pressure intensity, and the shape of the area of modified refractive index is defined by the geometry of the ultrasonic wave 22. Ultrasonic waves alternately create compression (positive lens) and rarefaction (negative lens) in the turbid medium 14. The refractive index increases marginally during compression and decreases marginally from the characteristic refractive index of the turbid medium 14. The volume of tissue, where ultrasonically induced gradient of refractive index is formed as a consequence of pressure changes, acts as an "acoustic lens" 24 whose optical power varies in time and space at the ultrasonic frequency. The strongest refractive index modulation occurs in the focal point 38 of the focused ultrasonic beam. Alternatively, where a planar ultrasonic beam is used, the refractive index modulation is proportional to acoustic pressure distribution within the ultrasonic beam and will have one or more compression and rarefaction regions within a fraction of the volume of interest where ultrasound beam is applied (insonified volume).

A fraction of light emitted from the florescent dye is transmitted through the ultrasonic focal point 38 of the acoustic lens 24 and is optically modulated at the ultrasonic frequency. The physical mechanism of the modulation is a deflection of the transmitted photon from its original direction by the acoustic lens. The strongest and/or weakest ultrasound-induced intensity variation on the detector occurs when the ultrasonic focal point (for focused ultrasonic beam) is located half way between the object of interest 16 and a plane of optical detection (detector). In other words, the emitted light 26 is tagged via the ultrasonic beam. Alternatively, the ultrasonic beam may be formed before the excitation light reaches the object of interest 16. The excitation light may be optically modulated before it excites the fluorescence in the object of interest, and therefore, the light emitted by the fluorescence in the object of interest will be modulated at the ultrasonic frequency of the ultrasonic generation system 20.

As will be appreciated by one skilled in the art, diffuse photons from an incoherent source may be modulated by refractive index changes in the focal region caused by the passage of focused ultrasonic energy. The strength of the diffuse photon modulation increases with increase in scattering coefficient and decreases with increase in absorption coefficient. Diffuse photon modulation is characterized by an inverse parabolic signature compared to the ballistic photon modulation which is characterized by a parabolic signature. In other words, the diffuse photon modulation is minimum when the acoustic focus is located mid-way between the source and the detector and maximum when the focus is close to the source or the detector while the ballistic photon modulation is maximum when the acoustic focus is located mid-way between the source and the detector and minimum when the focus is close to the source or the detector. The parabolic signatures or the inverse parabolic signatures allow for the localization of a fluorescent anomaly by sweeping the ultrasound focus across the sample for both near surface and deep tissue imaging. It should be noted that, in the geometric optic limit, photon modulation is a measure of the focusing effect of the acoustic lens created by the ultrasonic wave, while in the diffusive limit, the photon modulation is a measure of the defocusing effect of scattering. In other words, modulation of ballistic photons is a measure of their focusing by the acoustic lens while modulation of diffuse photons is a measure of their defocusing by scattering.

In certain embodiments, the ultrasonic beam 22 may provide acoustic guidance to the modulated light 26 by guiding the photons through an acoustically created waveguide. The size and shape of the focal region may be optimized to lend acoustic guidance to diffuse photons and strengthen the modulated signal several-fold. For example, for a 3 cm diameter circular or cylindrical phantom, there can be at least a thirty fold or 15 db increase in the peak signal strength of modulation by increasing the focal region of ultrasound from a spherical focus 3 mm across to a cylindrical line focus of 1 cm depth and 3 mm width. Further, the acoustic guidance may be optimally enhanced if the width of the focal region is comparable to the size of the fluorescent source. For example, a 1 cm wide and 1 cm long focal region enhances the modulation strength only by an additional 2 db compared to the 3 mm wide and 1 cm long acoustic guide. The modulated light 26 may be enhanced for improving the detection through a modification of the acoustic field that allows tunneling of the scattered photons and provides them acoustic guidance to the detector 36. The guidance of the diffuse photons may be more effective when the width of the tunnel is comparable to the size of the fluorescent source.

The modulated signal 26, e.g., the time varying intensity of light, is acquired and stored for further processing for each position of the ultrasonic focal spot during the scan. For example, when the acoustically modulated light reaches the boundary of the turbid medium (surface of the biological tissue), it can be detected using the optical detection system 28. A variety of optical detectors 36 may be employed for the detection of ultrasonic modulated light 26 such as, for example, a single optical detector (e.g., a photodetector), a photomultiplier tube (PMT), a photodiode; a photon counter, an image intensifier, arrays of photosensitive elements (array of photodetectors); or full field optical detectors such as charge-coupled device (CCD) cameras, a complementary metal oxide semiconductor (CMOS) device, avalanche photodiodes, a photo-refractive interferometer, and/or a full field speckle interferometer. The optical energy may be delivered to the detectors 36 via any suitable arrangement, such as free-space imaging optics such as a collection optic 32 and optical filter 34, optical fibers, fiber collimator, and/or through fiber bundles. An efficient detection of ultrasonic induced modulation requires blocking of excitation light that can be done using optical filtering techniques. One or more optical filters 34 may also be provided to reject light that is not fluorescent emission, and accept light that is fluorescent emission. In certain embodiments, the detection system 28 may also includes an amplifier (not shown) for amplifying the detected optical signal received from detector 36 and a bandpass filter (not shown) for filtering the amplified signal before being sent to the data processing system 30.

It should be noted that, as the ultrasonic focus is moved along a line that connects the fluorescent source and the optical detector, the peak signal for the ballistic photons or the minimum signal for the diffused photons would be detected when the focus is located midway between the fluorescent source and a fixed detector. For a fixed ultrasonic focus, the peak signal or the minimum signal would be detected as the detector is moved to align with the source and the focus such that the source and the detector are on either side of the focus. The measurements may be performed at a single or multiple detectors 36. It should be noted that, for detecting the peak or minimum signal as mentioned above, the ultrasonic focal spot should be located on the axis between fluorophore and the detector. Further, it should be noted that if the focal spot is not located on the axis between fluorophore and the detector (off-axis placement), the signals may be very weak.

The modulated optical signal 26 is detected using any suitable arrangement, such as one or more of the following techniques: (i) direct detection of the signal; (ii) a homodyne detection method wherein the gain of the optical signal is modulated at the ultrasonic frequency, and the phase between the optical gain and the ultrasound is swept over a range of angles; (iii) a heterodyne detection method wherein the gain of the optical signal is modulated at some frequency that is different than the ultrasonic frequency, and the amplitude of the signal at the side lobes is measured; (iv) a shuttering detection method that integrates the optical signal at a particular phase in the ultrasonic modulation over many acoustic cycles, wherein the optical signal is then integrated at one or more different phases over many acoustic cycles, and the modulated light signal is extracted by comparison of these integrated signals; or (v) a double cross correlation technique that performs a correlation analysis of the detected optical signal against the illumination input signal and the acoustic input signal to measure the amplitude of the signal for optimal noise rejection. The modulated light 26 may be detected in the time domain. Alternatively, if toneburst is used for excitation, the modulated light 26 may be detected in spatial domain. Such techniques should not, however, be considered as limiting of the overall approach taught herein.

In certain embodiments, the optical detection system 28 is configured to detect the modulated light 26 differentially. For example, in one embodiment the modulated light may be differentially detected based on the ultrasonic tagging. In another embodiment, the optical detection system may be configured to detect the ballistic photons, the snake-like photons and/or the diffused photons differentially based on the arrival time of the respective photons. As will be appreciated by one skilled in the art, the time taken by above-mentioned photons differs from one another because of their different paths in the turbid medium 14. Diffuse photons can travel several centimeters in the tissue before being absorbed, thereby enabling deep tissue imaging. A time domain optical detector 36 such as a photon counter may be used to detect the photons and thus measure the temporal point spread function for determining the strength of the ultrasonically modulated spectral components in the temporal signal as the ultrasonic beam 22 is moved across the field of view, thereby localizing the anomaly. Alternatively, PMT based detection using time-correlated single photon counting may be employed to provide high sensitivity, high dynamic range, high linearity and excellent signal-to-noise ratio.

As will be appreciated by one skilled in the art, multiple excitation sources may be used to illuminate the turbid medium. Similarly, to generate ultrasonic pulses at different locations and induce acoustic lens at varying angles, multiple transducers may be located at multiple points. Further, multiple detectors may be employed at different positions for acquiring the modulated light at the specified positions. Alternatively, a single detector coupled with multiple light collection and delivery systems may be used to acquire the modulated light.

The data collected by the optical detectors 36 will then be sent to the data processing system 30. As will be appreciated by one skilled in the art, the data processing system 30 may be implemented in various forms of hardware, software, firmware, special purpose processors, or a combination thereof. In one embodiment, the data processing system 30 may be implemented in software as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), a read only memory (ROM) and input/output (I/O) interface(s) such as a keyboard, a cursor control device (e.g., a mouse) and a display device (monitor).

The computer platform also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

Based on the detected signals, the data processing system 30 may localize the source of fluorescence, reconstruct a spatial distribution of the fluorescence in the turbid medium, and/or reconstruct an image of the object of interest. The image and the dye concentration can be reconstructed either through back-projection or through iterative approaches using the a priori information of the location of the anomalies. The reconstruction algorithm for the fluorescent optical image may be any suitable technique, such as one of the following conventional techniques: (i) solution by direct inversion of a linear description of the forward model; (ii) solution by iterative optimization of a nonlinear description of the forward model; or (iii) solution by direct solution of a nonlinear description of the forward model. Alternatively, the data processing system 30 may perform a Fourier analysis of a temporal point spread function of the modulated light at the ultrasonic frequency or its harmonics (integral multiple of the ultrasonic frequency) to measure the strength of early arriving ballistic photons as well as the relatively late arriving diffuse photons. Because the strength of diffuse photon modulations does not decrease with increase in scattering, the detection and use of the diffuse photons may allow for improved S/N ratio for deeper tissue imaging. The imaging system 10 may therefore perform both sub-surface and deeper tissue imaging with improved spatial resolution and sensitivity.

A diffusion approximation to the radiative transfer in a medium having varying refractive index is proposed as a theoretical model for the modulated light in the turbid medium. In a regime of scattering dominated propagation, photon transport of continuous wave light excitation within biological tissue with spatially varying refractive index can be described by the optical diffusion equation:

$$\nabla \cdot [D_x(\vec{r})\nabla \phi_x(\vec{r})] + \frac{2D_x(\vec{r})}{n_x(\vec{r})}\nabla n_x(\vec{r}) \cdot \nabla \phi_x(\vec{r}) - \mu_{a_x}(\vec{r})\phi_x(\vec{r}) = \frac{E}{4\pi} \quad (1)$$

where $\phi_x$ is the complex excitation fluence, $\mu_{ax}$ the absorption coefficient, $D_x$ is the optical diffusion coefficient ($D=1/\mu_s'$, where $\mu_s'$ is the reduced scattering coefficient), $n_x$ is the refractive index at position r, and E is the source distribution.

In a regime of scattering dominated propagation, photon transport of continuous wave light excitation within biological tissue can be described by the optical diffusion equation:

$$\nabla \cdot [D_x(\vec{r})\nabla \phi_x(\vec{r})] - \mu_{a_x}(\vec{r})\phi_x(\vec{r}) = 0 \quad (2)$$

where $\phi_x$ is the complex excitation fluence, $\mu_{ax}$ is the absorption coefficient, and $D_x$ is the optical diffusion coefficient at position r.

Transport of emission light in a scattering dominated propagation through a region of spatially varied refractive index is given by the diffusion equation:

$$\nabla \cdot [D_x(\vec{r})\nabla \phi_x(\vec{r})] + \frac{2D_x(\vec{r})}{n_x(\vec{r})}\nabla n_x(\vec{r}) \cdot \nabla \phi_x(\vec{r}) - \mu_{a_m}(\vec{r})\phi_x(\vec{r}) = \quad (3)$$

$$-\eta \mu_{a,x \to m}\phi_x(\vec{r})$$

where the source term on the right hand side represents the fluorescent emission source with a quantum yield η. The absorption coefficient of excitation light for absorption by fluorophore is $\mu_{a,x \to m}$, and absorption coefficient of emission light is $\mu_{am}$.

The synthetic excitation fluence on the boundary of tissue can be evaluated by using equation (2) in conjunction with Robin boundary condition:

$$\phi_x(\vec{r}) - 2AD_x(\vec{r})\frac{\partial \phi_x(r)}{\partial n} - S\delta(\vec{r},\vec{r}_s) = 0 \quad (4)$$

where S represents the flux density of a point source of light located at r on the boundary. Parameter A is the refractive index mismatch at the boundary. The excitation fluence replaces S in the calculation of emission fluence. A may be computed using an empirical approach, such as via the equation:

$$A = \frac{1+r_d}{1-r_d} \quad (5)$$

$$\text{where } r_d = -1.44n_{rel}^{-2} + 0.72n_{rel}^{-1} + 0.668 + 0.063n_{rel} \quad (6)$$

where $n_{rel}$ is the refractive index of the scattering medium with respect to the surrounding medium.

The synthetic emission fluence on the boundary of tissue can be evaluated by using equation (3) in conjunction with the Robin boundary condition appropriately modified to account for additional boundary of a closed region of modified refractive index in the interior of the medium. $A_{mod}$, the modified refractive index mismatch parameter A in the Robin boundary condition at the acoustically generated boundary is given by:

$$A_{mod} = \frac{A_1 A_2}{A_1 - A_2} \quad (7)$$

If $n_0$ represents the refractive index of the medium, $n_1$, the refractive index of the acoustically modified region then, $A_{mod}$ for the acoustic boundary is modeled as the difference between the refractive index mismatch between the medium with uniform $n_0$ and the surrounding and the refractive index mismatch between the medium with uniform $n_1$ and the surrounding.

As will be appreciated by one skilled in the art, the coupled optical diffusion equations may be solved through a Galerkin finite-element discretization of the solution space. For example, the 2D tissue phantom is subdivided into triangular elements in which $\phi_x$ and $\mu_{ax}$ are assumed to vary linearly. A global stiffness matrix K is assembled from local stiffness matrices for each element and the following matrix equation is solved computation of fluence for a point source/extended source represented by b:

$$K\phi_x = b \quad (8)$$

As will be appreciated by one skilled in the art, the modulation depth may be calculated using the diffuse photon transport model developed above. The defocusing is at a minimum when the acoustic lens is midway between the source of fluorescence and the detector. It should be noted that, both ballistic and diffuse signatures of ultrasonic modulation of incoherent light may help in the simultaneous localization of the anomaly (or feature of interest more generally) and determination of its optical properties. Further, as described above, optimally designed ultrasound beams may also be used to enhance diffuse photon modulation signal through acoustic guidance.

Figure 3:
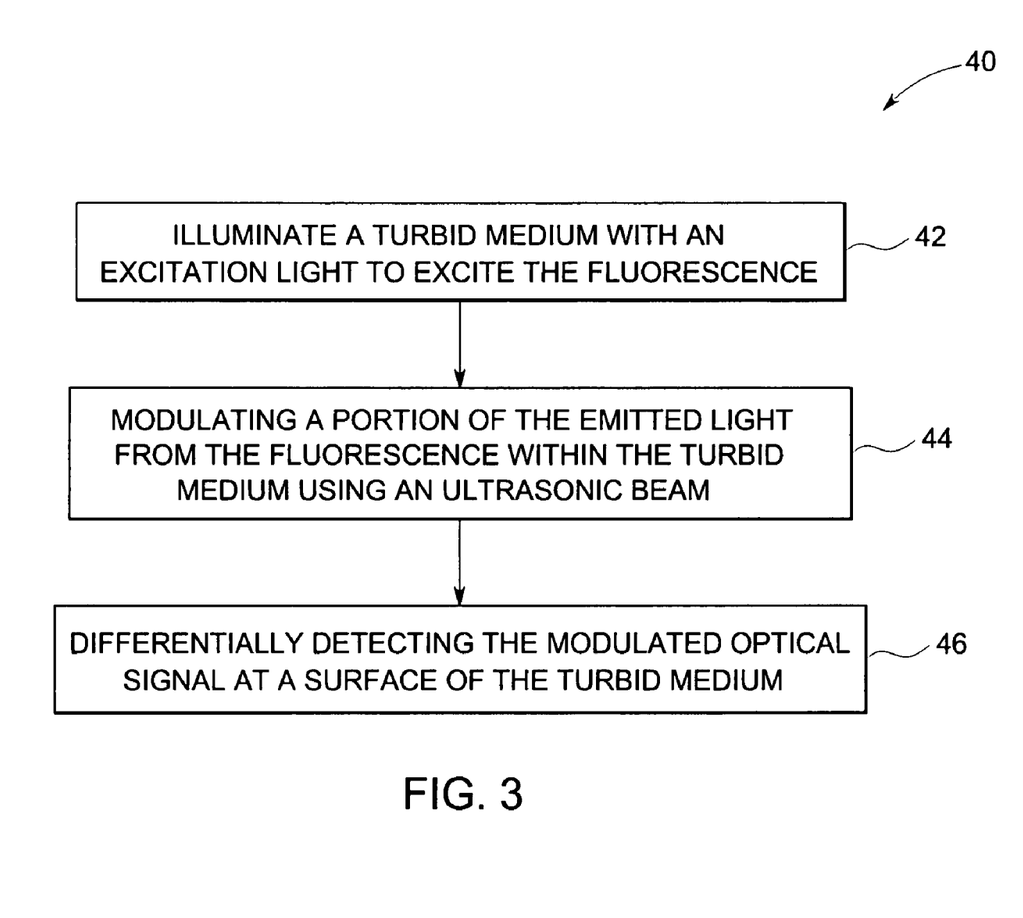
FIG. 3 is a flowchart illustrating a process for localizing fluorescence in a turbid medium.

Referring now to FIG. 3, exemplary control logic 40 for localizing fluorescence in a turbid medium via the acousto-optic imaging system such as imaging system 10 in accordance with aspects of the present technique is depicted via a flowchart. As illustrated in the flowchart, exemplary control logic 40 includes the steps of illuminating the turbid medium with an excitation light to excite the fluorescence at step 42, modulating a portion of the emitted light from the fluorescence within the turbid medium via an ultrasonic beam at step 44, and differentially detecting the modulated light at a surface of the turbid medium at step 46. The location of the fluorescent dye can then be determined from the detected data set obtained during ultrasonic scan over the volume of the biological tissue. When all the scans have been acquired, an image localizing the object of interest may be generated and displayed on the display or saved to memory. This may be done using, for example, the measured amplitude of the ultrasonically modulated signal and ultrasonic time-of-flight for each scan location; measured depth of modulation as a function of focal-spot-to-detector distance; or known focal-spot-to-detector geometry.

Figure 4:
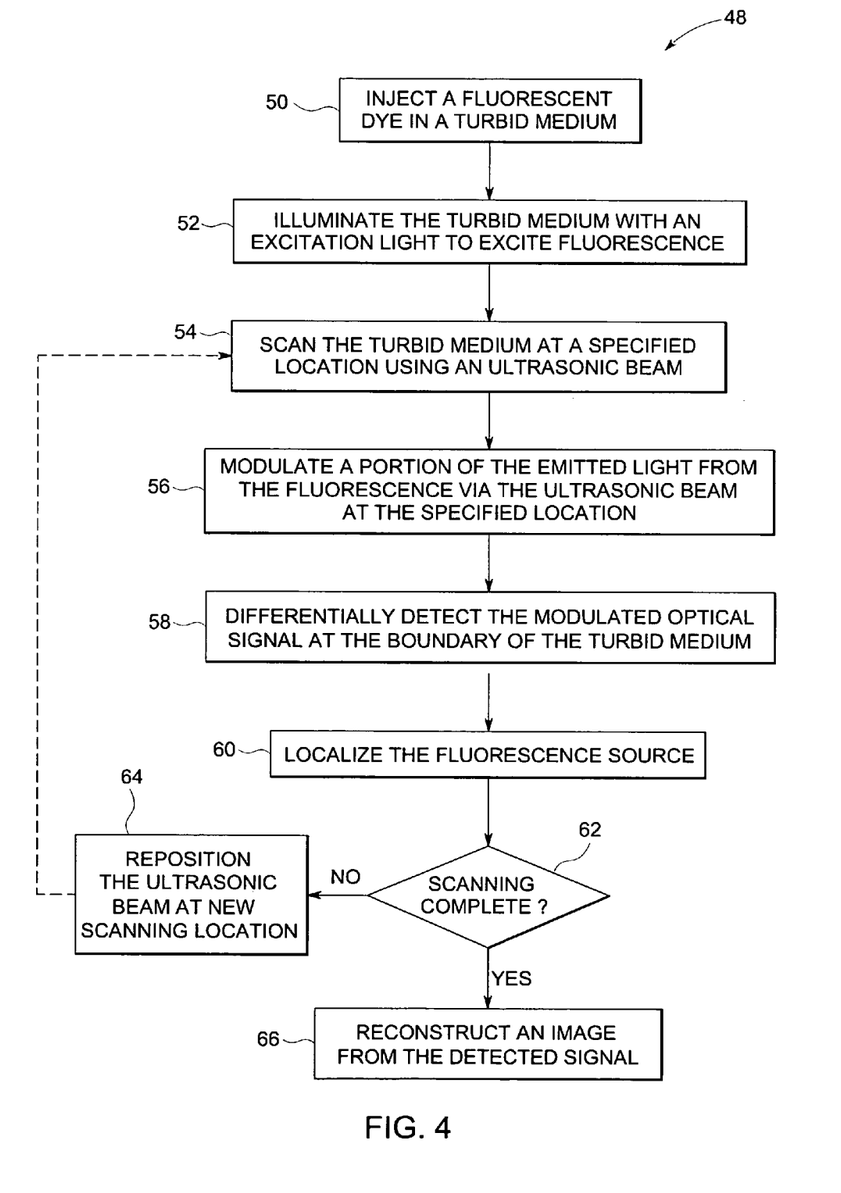
FIG. 4 is a flowchart illustrating a process for optical imaging in accordance with aspects of the present technique.

Referring now to FIG. 4, exemplary control logic 48 for imaging an object of interest via the acousto-optic imaging system such as imaging system 10 in accordance with aspects of the present technique is depicted via a flowchart. As illustrated in the flowchart, exemplary control logic 48 includes the steps of injecting a fluorescent dye or contrast agent in a turbid medium at step 50. The fluorescent contrast agent may preferentially bind to an object of interest 16. The control logic 48 further continues by illuminating the turbid medium with an excitation light to excite fluorescence at step 52, and scanning the turbid medium at a specific location via an ultrasonic beam at step 54. A portion of the emitted light from the fluorescence is modulated via the ultrasonic beam at the specified location at step 56. The control logic 48 further continues by deferentially detecting the modulated light at a boundary of the turbid medium at step 58, and localizing the fluorescence source at step 60. The control logic 48 then checks to determine whether the scanning is complete at step 62. If the scanning is not complete, the control logic 48 repositions the ultrasonic beam at new scanning location at step 64 and iterates the steps of scanning 54, modulating 56, differentially detecting 58 and localizing 60. Once the scanning is complete the control logic 48 reconstructs an image of the object of interest from the detected signal at step 66.

Figure 5:
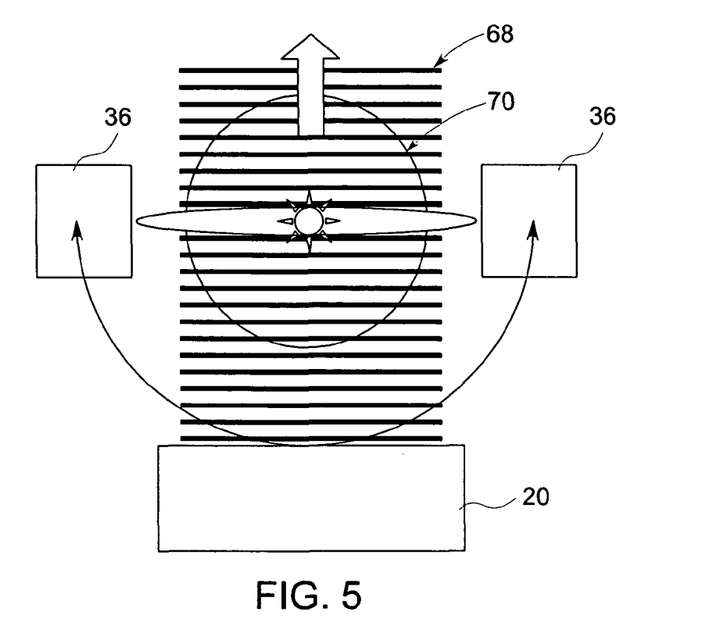
FIG. 5 is an exemplary imaging system for acousto-optic imaging using a planar ultrasound beam in accordance with one aspect of the present technique.
Figure 6:
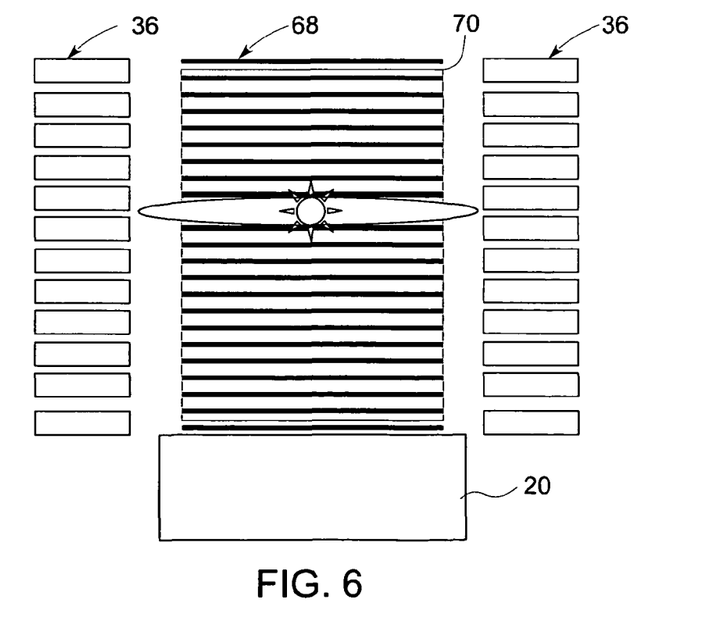
FIG. 6 is an exemplary imaging system for acousto-optic imaging using a planar ultrasound beam in accordance with another aspect of the present technique.

Additionally, in certain embodiments, an unfocused (planar) ultrasonic beam 68 may be employed to increase the speed of scanning over a volume of interest 70 as illustrated in FIGS. 5 and 6. As described above, in order to obtain a 3D image of fluorescent inclusions, the turbid medium is scanned with focused ultrasonic beam and the ultrasound-induced modulation of fluorescent light is measured for each position of the ultrasonic beam. The duration of the scan depends on the integration time for optical detection at each scan point, as well as on the number of scan-positions required to cover a volume. The use of an unfocused (planar) ultrasonic beam 68 that is wide enough to insonify the whole volume of interest 70 reduces the total acquisition time. Such wide ultrasonic beam 68 produces the ultrasound-induced modulation of light that can be detected only in a direction normal to the light-emitting source (e.g. light emitting feature within the turbid medium) with relatively reduced angular field of view (e.g., on order of 1 degree or less). The exact angular 'field of view' is a function of ultrasonic frequency and beam diameter. If the whole volume 70 of the sample is insonified with planar ultrasonic beam 68 the ultrasound-induced modulation of light will be detected when the optical detector and the light emitting source are generally located in the same plane normal to the ultrasonic beam axis.

Further, the modulated light is collected using, for example, fiber optics or free-space optics and delivered to one or more optical detectors 36. The detection configuration described above will allow one to identify the position of the light-emitting source along the axis of ultrasonic beam, which we will call the Z-axis. Exemplary optical detectors 36 may have the following configurations (1) a single optical detector coupled with multiple optical collectors (fiber bundles) that are moved along the Z-axis, (2) multiple detectors each coupled with multiple optical collectors that are placed along the length of the specimen (FIG. 5), or (3) a single or multiple optical detectors coupled with multiple optical collectors that cover the entire length of the Z-axis (FIG. 6). The third variation of the detection system allows one to determine the location of the optical source along the axis of ultrasonic beam without the need for mechanical scanning of the detectors along Z-axis. The ultrasonic pulses 68 would arrive at different locations along the Z-axis at different times. In this case the time of detection of the optical signal will encode the Z-coordinate of the light-emitting source. It is this fact that enables utilization of only one optical detector. A similar approach can be used to identify the position of the light-emitting source in the XY plane. Here again, the particular detector arrangement and technique should not be considered as limiting the invention claimed.

Figure 7:
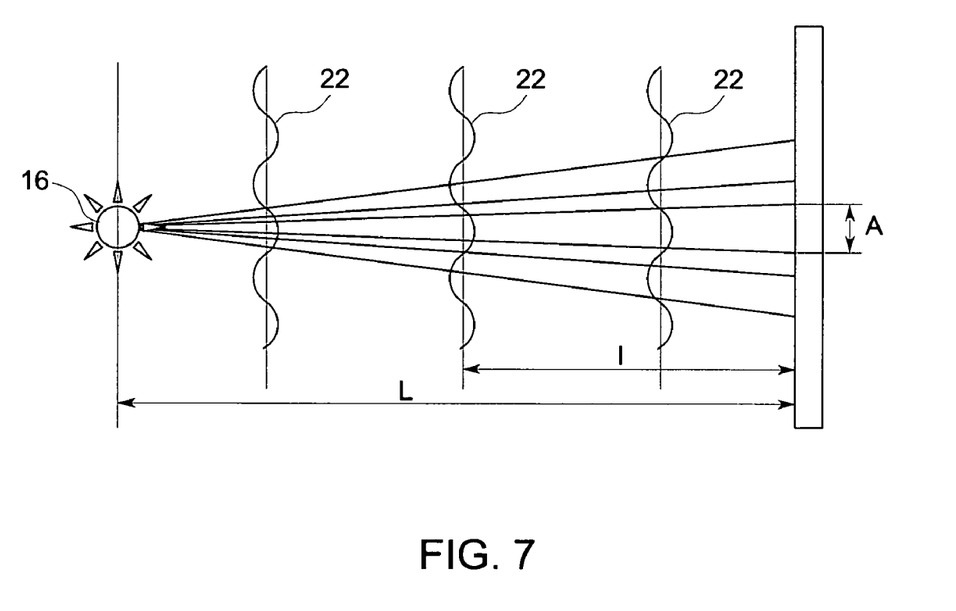
FIG. 7 illustrates a geometric model for analyzing the spatial parameters of ultrasound-induced intensity modulation on the surface of the specimen in accordance with one aspect of the present technique.

Another exemplary method of extracting the information about depth of the optical source without performing extended scans over multiple positions of the focused ultrasonic beam 22 is to analyze the spatial parameters of ultrasound-induced intensity modulation on the surface of the specimen. The depth of the optical source 16 may be calculated based on measurement of an ultrasound-induced intensity pattern for a single position of the ultrasonic beam. The geometric model for this measurement is shown in FIG. 7. The multiple lines from the fluorophore are angular sizes of a compression and rarefaction portion of ultrasonic cycle for three different positions of the ultrasonic beam. Ultrasonic waves of compression and rarefaction create a diffraction grating in their passage through the medium. The emitted light is diffracted while passing through the diffraction grating, thereby resulting in one or more diffraction fringes. Measuring the position of the source 16 in cases of extended or distributed sources will require a scanning of the ultrasonic beam along the depth and performing additional signal processing. In the case of an isolated optical source the depth, L, can be calculated as $L = A*1/(A-\lambda)$, where A is the width of ultrasound-induced "fringe", 1 is depth of ultrasonic beam, and $\lambda$ is ultrasonic wavelength. These features decrease the total acquisition time because the required number of sampling points is reduced.

Figure 8:
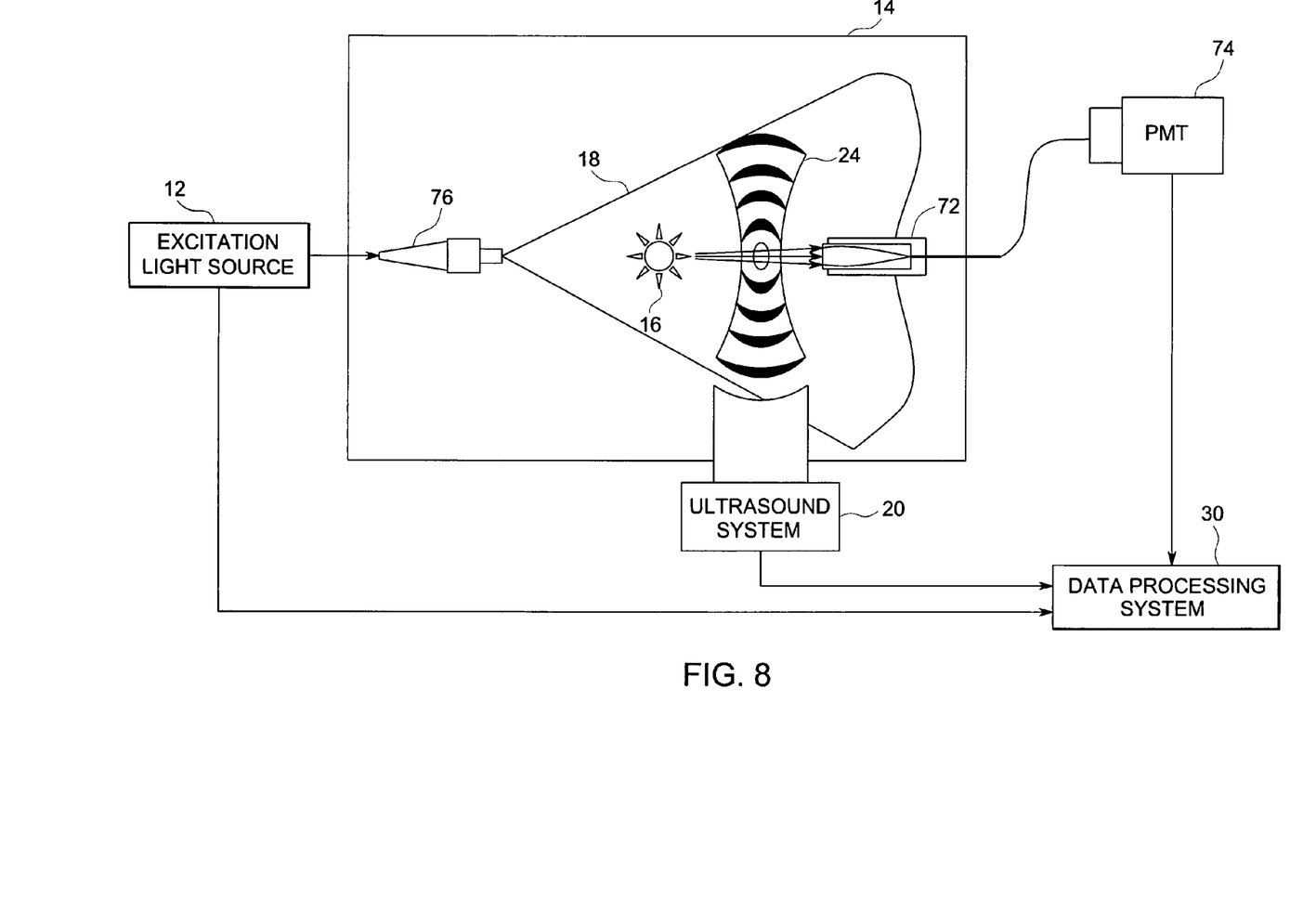
FIG. 8 is an exemplary imaging system for acousto-optic imaging using a photon detection system based on a fiber optic collimator for improving signal-to-noise ratio in accordance with aspects of the present technique.

Further, in certain embodiments, signal-to-noise ratio (SNR) may be improved by rejecting un-modulated multiple scattered photons using spatial filtering techniques. For example, SNR may also be improved by using a photon detection system based on fiber optic collimator 72 as illustrated in FIG. 8. Improving the SNR reduces the required integration time for each point, and therefore reduces the total scan time. It is known that different ballistic photon imaging techniques can be used to localize a light-emitting source in a scattering medium with sub-millimeter spatial resolution. However ballistic photon imaging techniques lack the ability to measure the depth of the source, and in order to localize the source several measurements from different angles have to be made, and standard back-projection algorithms employed. Alternatively, a method of adding axial or depth discrimination capability to conventional imaging techniques (based solely on acquiring information from ballistic photons) by a scanning focused ultrasonic beam along the optical axis of the optical collimator 72 may be employed. As will be appreciated by one skilled in the art, the fiber optic collimator 72 allows the photodetector or PMT 74 to detect only the photons that travel parallel to its optical axis. Several fiber collimators and ultrasonic transducers may be used to decrease the total scanning time. In the illustrated embodiment, the turbid medium is illuminated via fiber optic illuminator 76.

As will be appreciated by one skilled in the art, the techniques described in various embodiments discussed above provides for increased optical image resolution, simultaneous anatomical imaging (using ultrasonic scan data) and functional imaging (using optical data), decreased optical reconstruction complexity and required computation time, while utilizing non-ionizing radiation. Additionally, the techniques provide for improved scanning speed by reducing the total acquisition time and improved SNR by addition of depth discrimination capability to conventional ballistic photon imaging techniques.

In the event of sufficient ballistic photon count, the minimum defocusing effect of the diffuse photons may lead to a relatively easy detection of a classical parabolic signature of modulated signal to help in localizing a continuous wave source. However, when ballistic photon budget is very low as in the case of higher scattering and larger depths, it may be possible to use the temporal point spread function of an ultra-short laser pulse modulated by the ultrasonic wave and its component at the ultrasonic frequency to simultaneously localize a feature of interest and determine its optical properties. As will be appreciated by one skilled in the art, such optical properties may provide a way to discriminate between normal and diseased tissue. The imaging system described in the various embodiments discussed above is therefore capable of acquiring anatomical as well as functional information non-invasively in a single acousto-optic measurement and thereby provide improved diagnosis as well as early detection of disease.

Further, the techniques described in the embodiments discussed above combine the spatial resolution of ultrasound with the sensitivity of fluorescence optical imaging for both sub-surface and deep tissue imaging. The modulation of multiply scattered incoherent photons in the presence of ultrasound may be used to boost the strength of ultrasonic modulation of incoherent photons for high scattering and greater depths of tissue in order to improve the spatial resolution of fluorescent optical imaging through ultrasonic tagging by the simultaneous application of NIR light and ultrasound to image tissue. The techniques may further be used to test and speed up fluorescent dye development, and may be used in pre-clinical setting for accelerated drug development and therapy.

It should also be noted that applications of the present techniques are not limited to medical imaging. Rather, any imaging or material characterization application may benefit from these techniques, particularly where at least some optical transmission is possible in order to permit focusing and detection of photons as discussed above.

The embodiments illustrated above may comprise a listing of executable instructions for implementing logical functions. The listing can be embodied in any computer-readable medium for use by or in connection with a computer-based system that can retrieve, process and execute the instructions. Alternatively, some or all of the processing may be performed remotely by additional computing resources.

In the context of the present technique, the computer-readable medium may be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for localization of fluorescence in a medium, the method comprising:
   illuminating the medium with an excitation light to excite the fluorescence resulting in an emission of light from the fluorescence;
   modulating a portion of the emitted light at a determined location that is away from the location of the fluorescence within the medium via an ultrasonic beam, wherein the determined location is between the location of the fluorescence and a surface of the medium; and
   differentially detecting the modulated light at the surface of the medium based on differences in a predetermined parameter,
   wherein the step of modulating is performed by an ultrasonically induced gradient of refractive index of the medium.

2. The method of claim 1, wherein the excitation light is an ultra-short laser pulse or a sequence of ultra-short laser pulses.

3. The method of claim 1, wherein the step of modulating comprises modifying a direction of the portion of the emitted light from the fluorescence via the ultrasonic beam.

4. The method of claim 3, wherein the predetermined parameter is the modified direction.

5. The method of claim 1, wherein the portion of the emitted light from the fluorescence comprises ballistic photons, snake-like photons, and/or diffused photons.

6. The method of claim 5, wherein thepredetermined parameter is presence of the ballistic photons, snake-like photons and/or the diffuse photons based on an arrival time of respective photons.

7. The method of claim 1, further comprising providing acoustic guidance to the modulated light via the ultrasonic beam.

8. The method of claim 1, further comprising performing Fourier analysis of a temporal point spread function of the modulated light at a frequency that is a multiple of the frequency of the ultrasonic beam.

9. The method of claim 1, further comprising reconstructing a spatial distribution of the fluorescence in the medium from the detected signal.

10. The method of claim 9, wherein the step of reconstructing further comprises scanning a volume of the medium with the focused ultrasonic beam and detecting the modulated light for each scanning location.

11. The method of claim 1, further comprising scanning a volume of the medium with a planar ultrasonic beam.

12. The method of claim 1, wherein the illumination with the excitation light is in a continuous wave mode, a pulsed wave mode or an intensity modulated wave mode.

13. The method of claim 1, wherein the ultrasonically induced gradient of the refractive index acts as an acoustic lens, and an optical power of the acoustic lens varies in time and space at the frequency of the ultrasonic beam.

14. A method of imaging, the method comprising:
   illuminating a medium with an excitation light to excite fluorescence resulting in an emission of light from the fluorescence;
   scanning the medium at a plurality of determined locations via an ultrasonic beam;
   modulating a portion of the emitted light at each of the plurality of determined locations that are away from the location of the fluorescence within the medium via the ultrasonic beam, wherein the plurality of determined locations are between the location of the fluorescence and a boundary of the medium;
   differentially detecting the modulated light at the boundary of the medium based on differences in a predetermined parameter; and
   reconstructing an image from the detected signal,
   wherein the step of modulating is performed by an ultrasonically induced gradient of refractive index of the medium.

15. The method of claim 14, further comprising injecting a fluorescent agent in the medium.

16. The method of claim 14, wherein the step of modulating is performed by an ultrasonically induced gradient of pressure.

17. The method of claim 16, wherein the acoustic or ultrasonic pressure varies with time and space.

18. An acousto-optic imaging system for localization of fluorescence in a medium, the system comprising:
   an excitation light source for illuminating the medium with an excitation light;
   a fluorescent agent within a preselected region of the medium for absorbing the excitation light and emitting light in a near infrared spectral region via fluorescence;
   an ultrasonic scanning system for generating ultrasonic beam, wherein the ultrasonic beam modulates a portion of the emitted light at a determined location that is away from the fluorescent agent by forming an ultrasonically induced gradient of refractive index, wherein the determined location is between the location of the fluorescence within the medium and a surface of the medium; and
   an optical detection system for differentially detecting the modulated light based on differences in a predetermined parameter.

19. The system of claim 18, further comprising a data processing system configured to generate a spatial distribution of the fluorescence in the medium or to generate an image based on the detected modulated light.

20. The system of claim 19, wherein the data processing system is configured to perform Fourier analysis of a temporal point spread function of the modulated light at a frequency that is a multiple of the frequency of the ultrasonic beam.

21. The system of claim 18, wherein the excitation light source is a laser, laser diode, light emitting diode or a lamp.

22. The system of claim 18, wherein the fluorescent agent is cyanine, squarilium, croconium, merocyanine or oxonol dye molecule, lanthanide metal chelate, quantum dot, metal nano-cluster, Indocyanine green, a member of the Cy family of dyes, IR-78 dye, peptide or a fluorophore that emits in the near infrared region of light.

23. The system of claim 18, wherein the ultrasonic scanning system comprises at least one of a piezoelectric ultrasound transducer, a capacitive ultrasound transducer, an ultrasonic scanning phase array, a laser photo-acoustic generator, or combinations thereof.

24. The system of claim 18, wherein the optical detection system further comprises:
   a light collection and delivery system for collecting the emitted light;
   at least one optical filter for filtering the light and allowing transmission of fluorescent emission; and
   a detector for converting optical signals to electrical signals capable of being read by a data processing system.

25. The system as in claim 24, wherein the light collection and delivery system includes at least one of optical fiber or a fiber collimator for delivering collected light from the medium to the detector.

26. The system as in claim 24, wherein the detector comprise at least one of a photodectector, a photomultiplier tube (PMT), an image intensifier, a charge-coupled device, a photon counter, an array of photosensitive elements, a complementary metal oxide semiconductor device, photodiodes, avalanche photodiodes, a photo-refractive interferometer, a full field speckle interferometer, or a combination thereof.

27. The system of claim 18, wherein the ultrasonic beam modulates the portion of the emitted light by modifying a direction of the portion of the emitted light.

28. The system of claim 27, wherein the predetermined parameter is the modified direction.

29. The system of claim 18, wherein the portion of the emitted light from the fluorescence comprises ballistic photons, snake-like photons and/or diffused photons.

30. The system of claim 29, wherein the predetermined parameter is presence of the ballistic photons, snake-like photons and/or the diffuse photons based on an arrival time of respective photons.

31. The system of claim 18, wherein the ultrasonic scanning system provides acoustic guidance to the modulated light.

32. The system of claim 18, wherein the ultrasonic scanning system scans a volume of the medium with a planar ultrasonic beam.

33. An imaging system, comprising:
   an excitation light source for illuminating a medium with an excitation light;
   a fluorescent agent within a preselected region of the medium for absorbing the excitation light and emitting light in a near infrared spectral region via fluorescence;
   an ultrasonic scanning system for:
      generating ultrasonic beam, wherein the ultrasonic beam scans the medium at a plurality of determined locations and modulates a portion of the emitted light at the plurality of determined locations that are away from the fluorescent agent by forming an ultrasonically induced gradient of refractive index;

an optical detection system for differentially detecting the modulated light based on differences in a predetermined parameter; and
a data processing system for reconstructing an image from the detected signal,
wherein the plurality of determined locations are between the location of the fluorescence and the optical detection system,
wherein the ultrasonically induced gradient of the refractive index acts as an acoustic lens, and an optical power of the acoustic lens varies in time and space at the frequency of the ultrasonic beam.

* * * * *

UNITED STATES PATENT AND TRADEMARK OFFICE
CERTIFICATE OF CORRECTION

PATENT NO.       : 8,103,329 B2                                          Page 1 of 1
APPLICATION NO.  : 11/254266
DATED            : January 24, 2012
INVENTOR(S)      : Fomitchov et al.

It is certified that error appears in the above-identified patent and that said Letters Patent is hereby corrected as shown below:

In Column 14, Line 59, in Claim 6, delete "thepredetermined" and insert -- the predetermined --, therefor.

In Column 16, Line 31, in Claim 26, delete "photodectector," and insert -- photodetector, --, therefor.

Signed and Sealed this
Second Day of October, 2012

David J. Kappos
*Director of the United States Patent and Trademark Office*